(12) United States Patent
Rizk

(10) Patent No.: US 7,641,825 B2
(45) Date of Patent: Jan. 5, 2010

(54) METHOD OF MAKING A POLYHYDROXYALKANOATE FILAMENT

(75) Inventor: Said Rizk, Londonderry, NH (US)

(73) Assignee: Tepha, Inc., Cambridge, MA (US)

( * ) Notice: Subject to any disclaimer, the term of this patent is extended or adjusted under 35 U.S.C. 154(b) by 445 days.

(21) Appl. No.: 11/193,580

(22) Filed: Jul. 29, 2005

(65) Prior Publication Data

US 2006/0058470 A1    Mar. 16, 2006

Related U.S. Application Data

(60) Provisional application No. 60/598,296, filed on Aug. 3, 2004.

(51) Int. Cl.
*D01D 5/084*     (2006.01)
*D01D 5/16*      (2006.01)
*D01F 6/62*      (2006.01)
*D02J 1/22*      (2006.01)

(52) U.S. Cl. .............. 264/28; 264/103; 264/210.5; 264/210.6; 264/210.8; 264/211.17; 264/235.6; 264/342 RE

(58) Field of Classification Search .............. 264/28, 264/103, 210.5, 210.6, 210.8, 211.17, 235.6, 264/342 RE
See application file for complete search history.

(56) References Cited

U.S. PATENT DOCUMENTS

| | | | |
|---|---|---|---|
| 3,598,122 A | 8/1971 | Zaffaroni et al | |
| 3,598,123 A | 8/1971 | Zaffaroni et al. | |
| 3,731,683 A | 5/1973 | Zaffaroni | |
| 3,797,494 A | 3/1974 | Zaffaroni | |
| 3,982,543 A | 9/1976 | Schmitt et al. | 128/335.5 |
| 4,031,894 A | 6/1977 | Urquhart et al. | |
| 4,201,211 A | 5/1980 | Chandrasekaran et al. | |
| 4,205,399 A | 6/1980 | Jamiolkowski | |
| 4,286,592 A | 9/1981 | Chandrasekaran | |
| 4,314,557 A | 2/1982 | Chandrasekaran | |
| 4,379,454 A | 4/1983 | Campbell et al. | |
| 4,435,180 A | 3/1984 | Leeper | |
| 4,537,738 A | 8/1985 | Holmes | |
| 4,559,222 A | 12/1985 | Enscore et al. | |
| 4,573,995 A | 3/1986 | Chen et al. | |
| 4,588,580 A | 5/1986 | Gale et al. | |
| 4,603,070 A | 7/1986 | Steel et al. | |
| 4,645,502 A | 2/1987 | Gale et al. | |
| 4,648,978 A | 3/1987 | Makinen et al. | 210/759 |
| 4,664,655 A | 5/1987 | Orentreich et al. | |
| 4,704,282 A | 11/1987 | Campbell et al. | |
| 4,711,241 A | 12/1987 | Lehmann | 128/335.5 |
| 4,758,234 A | 7/1988 | Orentreich et al. | |
| 4,788,062 A | 11/1988 | Gale et al. | |
| 4,792,336 A | 12/1988 | Hlavacek et al. | |
| 4,816,258 A | 3/1989 | Nedberge et al. | |
| 4,826,493 A | 5/1989 | Martini et al. | 604/327 |
| 4,849,226 A | 7/1989 | Gale | |
| 4,853,226 A | 8/1989 | Machida et al. | |
| 4,856,188 A | 8/1989 | Sibalis | |
| 4,880,592 A | 11/1989 | Martini et al. | 264/514 |
| 4,908,027 A | 3/1990 | Enscore et al. | |
| 4,910,145 A | 3/1990 | Holmes et al. | 435/259 |
| 4,938,763 A | 7/1990 | Dunn et al. | |
| 4,943,435 A | 7/1990 | Baker et al. | |
| 5,002,067 A | 3/1991 | Berthelsen et al. | |
| 5,026,381 A | 6/1991 | Li | |
| 5,032,638 A | 7/1991 | Wang et al. | 524/400 |
| 5,041,100 A | 8/1991 | Rowland et al. | |
| 5,085,629 A | 2/1992 | Goldberg et al. | |
| 5,124,371 A | 6/1992 | Tokiwa et al. | |
| 5,128,144 A | 7/1992 | Korsatko-Wabnegg et al. | 424/464 |
| 5,171,308 A * | 12/1992 | Gallagher et al. | 604/365 |
| 5,204,382 A | 4/1993 | Wallace et al. | |
| 5,236,431 A | 8/1993 | Gogolewski et al. | 606/72 |
| 5,245,023 A | 9/1993 | Peoples et al. | 536/23.2 |
| 5,250,430 A | 10/1993 | Peoples et al. | 435/232 |
| 5,271,961 A | 12/1993 | Mathiowitz et al. | 427/213.31 |
| 5,278,201 A | 1/1994 | Dunn et al. | |

(Continued)

FOREIGN PATENT DOCUMENTS

CA    2307637    5/1999

(Continued)

OTHER PUBLICATIONS

Clavijo-Alvarez, et al. "Comparison of biodegradable conduits within aged rat sciatic nerve defects," *Plast Reconstr Surg.* 119(6):1839-51(2007).

Kishida, et al. "Formulation assisted biodegradeable polymer matrices" *Chemical and Pharmaceutical Bulletin, JP Pharm Society of Japan.* 37(7):1954-1956(1989).

Pouton, et al. "Biosynthetic polyhydroxyalkanoates and their potentials in drug delivery" *Adv. Drug Deliv. Rev.* 18(18)133-162.

Schlosshauer, "Synthetic nerve guide implants in humans: a comprehensive survey." *Neurosurgery* 59:740-748 (2006).

Agostini, et al., "Synthesis and Characterization of Poly-β-Hydroxybutyrate. I. Synthesis of Crystalline DL Poly-β-Hydroxybutyrate from DL- β-Butyrolactone," *Polym. Sci.*, Part A-1, 9:2775-87 (1971).

(Continued)

*Primary Examiner*—Leo B Tentoni
(74) *Attorney, Agent, or Firm*—Pabst Patent Group LLP

(57) ABSTRACT

Absorbable polyester fibers, braids, and surgical meshes with improved handling properties have been developed. These devices are preferably derived from biocompatible copolymers or homopolymers of 4-hydroxybutyrate. These devices provide a wider range of in vivo strength retention properties than are currently available and have a decreased tendency to curl, in the preferred embodiment, due to the inclusion of relaxation and annealing steps following methods are characterized by the following physical properties: (i) elongation to break from about 17% to about 85% (ii) Young's modulus of less than 350,000 psi, (iii) knot to straight ratio (knot strength/tensile strength) of 55-80% or (iv) load at break from 1100 to 4200 grams.

7 Claims, No Drawings

U.S. PATENT DOCUMENTS

| | | | |
|---|---|---|---|
| 5,278,202 A | 1/1994 | Dunn et al. | |
| 5,278,256 A | 1/1994 | Bellis | |
| 5,292,860 A | 3/1994 | Shiotani et al. | 528/361 |
| 5,306,286 A | 4/1994 | Stack et al. | |
| 5,334,698 A | 8/1994 | Witholt et al. | 528/354 |
| 5,412,067 A | 5/1995 | Shinoda et al. | |
| 5,443,458 A | 8/1995 | Eury | |
| 5,468,253 A | 11/1995 | Bezwada et al. | 606/230 |
| 5,480,394 A | 1/1996 | Ishikawa | |
| 5,480,794 A | 1/1996 | Peoples et al. | 435/23.2 |
| 5,489,470 A | 2/1996 | Noda | 428/286 |
| 5,502,116 A | 3/1996 | Noda | 525/415 |
| 5,502,158 A | 3/1996 | Sinclair et al. | 528/354 |
| 5,512,669 A | 4/1996 | Peoples et al. | 36/23.2 |
| 5,516,565 A | 5/1996 | Matsumoto | |
| 5,516,883 A | 5/1996 | Hori et al. | 528/354 |
| 5,534,432 A | 7/1996 | Peoples et al. | 435/240.4 |
| 5,536,564 A | 7/1996 | Noda | 428/280 |
| 5,550,173 A | 8/1996 | Hammond et al. | 523/122 |
| 5,551,954 A | 9/1996 | Buscemi et al. | |
| 5,563,239 A | 10/1996 | Hubbs et al. | 528/361 |
| 5,584,885 A | 12/1996 | Seckel | |
| 5,614,576 A | 3/1997 | Rutherford et al. | |
| 5,625,030 A | 4/1997 | Williams et al. | |
| 5,629,077 A | 5/1997 | Turnlund et al. | |
| 5,635,215 A | 6/1997 | Boschetti et al. | |
| 5,646,217 A | 7/1997 | Hammond | |
| 5,648,100 A | 7/1997 | Boschetti et al. | |
| 5,670,161 A | 9/1997 | Healy et al. | |
| 5,703,160 A | 12/1997 | Dehennua et al. | |
| 5,705,187 A | 1/1998 | Unger | 424/450 |
| 5,709,854 A | 1/1998 | Griffiths-Cima et al. | |
| 5,711,933 A | 1/1998 | Bichon et al. | 424/9.52 |
| 5,728,752 A | 3/1998 | Scopelianos et al. | |
| 5,735,863 A | 4/1998 | Della Valle | |
| 5,753,364 A | 5/1998 | Rutherford et al. | |
| 5,753,708 A | 5/1998 | Koehler et al. | |
| 5,789,536 A | 8/1998 | Liggat et al. | 528/503 |
| 5,811,272 A | 9/1998 | Snell et al. | 435/135 |
| 5,814,071 A | 9/1998 | McDevitt et al. | |
| 5,814,599 A | 9/1998 | Mitragotri et al. | |
| 5,824,333 A | 10/1998 | Scopelianos et al. | |
| 5,824,751 A | 10/1998 | Hori et al. | |
| 5,834,582 A | 11/1998 | Sinclair et al. | |
| 5,840,331 A | 11/1998 | Van Cauter et al. | |
| 5,842,477 A | 12/1998 | Naughton et al. | |
| 5,855,619 A | 1/1999 | Caplan et al. | |
| 5,874,040 A * | 2/1999 | Liggat et al. | 264/346 |
| 5,876,452 A | 3/1999 | Athanasiou et al. | |
| 5,876,455 A | 3/1999 | Harwin | |
| 5,879,322 A | 3/1999 | Lattin et al. | |
| 5,919,478 A | 7/1999 | Landrau et al. | |
| 5,935,506 A | 8/1999 | Schmitz et al. | |
| 5,990,162 A | 11/1999 | Scharf | |
| 5,994,478 A | 11/1999 | Asrar et al. | |
| 6,056,970 A | 5/2000 | Greenawalt et al. | |
| 6,119,567 A | 9/2000 | Schindler et al. | |
| 6,214,387 B1 | 4/2001 | Berde et al. | |
| 6,245,537 B1 | 6/2001 | Williams et al. | 435/135 |
| 6,316,262 B1 | 11/2001 | Huisman et al. | 435/490 |
| 6,323,010 B1 | 11/2001 | Skraly et al. | 435/135 |
| 6,454,811 B1 | 9/2002 | Sherwood et al. | 623/23.76 |
| 6,514,515 B1 | 2/2003 | Williams | 424/424 |
| 6,548,569 B1 | 4/2003 | Williams et al. | 523/124 |
| 6,555,123 B2 | 4/2003 | Williams et al. | |
| 6,600,010 B2 | 7/2003 | Mao et al. | |
| 6,610,764 B1 | 8/2003 | Martin et al. | |
| 6,623,749 B2 | 9/2003 | Williams et al. | |
| 6,656,489 B1 | 12/2003 | Mahmood et al. | 424/426 |
| 6,680,046 B1 | 1/2004 | Boschetti | |
| 6,770,356 B2 * | 8/2004 | O'Donnell et al. | 428/297.4 |
| 6,838,493 B2 | 1/2005 | Williams et al. | |
| 6,867,247 B2 | 3/2005 | Williams et al. | |
| 6,878,248 B2 | 4/2005 | Signer et al. | |
| 6,878,758 B2 | 4/2005 | Martin et al. | |
| 7,179,883 B2 | 2/2007 | Williams et al. | |
| 7,244,442 B2 | 7/2007 | Williams et al. | |
| 7,268,205 B2 | 9/2007 | Williams et al. | |
| 2002/0028243 A1 | 3/2002 | Masters | |
| 2002/0156150 A1 | 10/2002 | Williams et al. | |
| 2002/0173558 A1 | 11/2002 | Williams et al. | |
| 2003/0091803 A1 * | 5/2003 | Bond et al. | 428/292.1 |
| 2003/0185896 A1 | 10/2003 | Bruiser et al. | |
| 2003/0211131 A1 | 11/2003 | Martin et al. | |
| 2004/0234576 A1 * | 11/2004 | Martin et al. | 424/426 |
| 2005/0107505 A1 * | 5/2005 | Shinoda et al. | 524/321 |
| 2005/0267516 A1 | 12/2005 | Soleimani | |
| 2006/0058470 A1 | 3/2006 | Rizk | |

FOREIGN PATENT DOCUMENTS

| | | |
|---|---|---|
| CA | 2259098 | 7/1999 |
| CA | 2298421 | 2/2000 |
| DE | 39 37 649 | 5/1991 |
| EP | 0 258 781 | 3/1988 |
| EP | 0 344 704 | 12/1989 |
| EP | 0 349 505 | 3/1990 |
| EP | 0 423 484 | 4/1991 |
| EP | 0 432 443 | 6/1991 |
| EP | 0 452 111 | 10/1991 |
| EP | 0 507 554 | 10/1992 |
| EP | 4-326932 | 11/1992 |
| EP | 5-023189 | 2/1993 |
| EP | 0 429 403 | 5/1994 |
| EP | 0 601 885 | 6/1994 |
| EP | 0 628 586 | 12/1994 |
| EP | 0 754 467 | 1/1997 |
| EP | 7 754 467 | 1/1997 |
| EP | 1130043 | 9/2001 |
| EP | 1266984 | 12/2002 |
| GB | 2166354 | 5/1986 |
| JP | 62-209144 | 9/1987 |
| JP | 03-187386 | 8/1991 |
| JP | 04-292619 | 10/1992 |
| JP | 04-326932 | 11/1992 |
| JP | 4-326932 | 11/1992 |
| JP | 5-023189 | 2/1993 |
| JP | 5-194141 | 11/1993 |
| JP | 06-264306 | 9/1994 |
| JP | 06-336523 | 12/1994 |
| JP | 7 275 344 | 10/1995 |
| JP | 07-275344 | 10/1995 |
| JP | 08-089264 | 4/1996 |
| JP | 0 821 216 | 8/1996 |
| JP | 09-098793 | 4/1997 |
| JP | 09-507091 | 7/1997 |
| JP | 2000220032 | 8/2000 |
| WO | WO 92/18164 | 10/1992 |
| WO | WO 93/05824 | 4/1993 |
| WO | WO 93/20134 | 10/1993 |
| WO | WO 94/02184 | 2/1994 |
| WO | WO 94/06886 | 3/1994 |
| WO | WO 95/03356 | 2/1995 |
| WO | WO 95/17216 | 6/1995 |
| WO | WO 95/20614 | 8/1995 |
| WO | WO 95/20615 | 8/1995 |
| WO | WO 95/20621 | 8/1995 |
| WO | WO 95/23250 | 8/1995 |
| WO | WO 95/33874 | 12/1995 |
| WO | WO 96/00263 | 1/1996 |
| WO | WO 96/08535 | 3/1996 |
| WO | WO 96/18420 | 6/1996 |
| WO | WO 96/21427 | 7/1996 |
| WO | WO 96/40304 | 12/1996 |

| WO | WO 97/04036 | 2/1997 |
| WO | WO 97/07153 | 2/1997 |
| WO | WO 97/15681 | 5/1997 |
| WO | WO 97/30042 | 8/1997 |
| WO | WO 98/04292 | 2/1998 |
| WO | WO 98/39453 | 9/1998 |
| WO | WO 98/48028 | 10/1998 |
| WO | WO 98/51812 | 11/1998 |
| WO | WO 99/11196 | 3/1999 |
| WO | WO 99/14313 | 3/1999 |
| WO | WO 99/32536 | 7/1999 |
| WO | WO 99/35192 | 7/1999 |
| WO | WO 00/51662 | 9/2000 |
| WO | WO 00/56376 | 9/2000 |
| WO | WO 01/10421 | 2/2001 |
| WO | WO 01/15671 | 3/2001 |
| WO | WO 01/19361 | 3/2001 |
| WO | WO 02/085983 | 10/2002 |
| WO | WO 2004/101002 | 11/2004 |

OTHER PUBLICATIONS

Akhtar, "Physiomechanical Properties of bacterial P(HB-HV) Polyesters and Their Uses in drug Delivery", The British Library Document Supply Centre, UMI, (1990).

Anderson, et al., "Occurrence, Metabolism, metabolic Role, and Industrial Uses of bacterial Polyhydroxyalkanoates", *Microbiological Reviews*, pp. 450-472 (1990).

Bailey, "Free radical ring-opening polymerization", *J. Polym. Preprints*, 25:210-11 (1984).

Bailey, et al., "Synthesis of Poly-ϵ-caprolactone via a free radical mechanism. Free radical ring-opening polymerization of 2-methylene-1,3-dioxepane", *J. Polym. Sci. Polym. Chem.*, 20:3021-30 (1982).

Berger, et al., "PHB recovery by hypochlorite digestion of non-PHB biomass", *Biotechnonology Techniques*, 3(4):227-232 (1989).

Boeree, et al., "Development of a degradable composite for orthopaedic use: mechanical evaluation of an hydroxyapatite-polyhydroxybutyrate composite material", *Biomaterials*, 14(10):793-6 (1993).

Braunegg, et al., "Polyhydroxyalkanoates, biopolyesters from renewable resources: physiological and engineering aspects", *J. Biotech.*, 65: 127-161 (1998).

Bruhn & Müller, "Preparation and characterization of spray-dried Poly(DL-Lactide) Micro Spheres", *Proceed. Intern. Symp. Control. Rel. Bioact. Mater.*, 18:668-69 (1991).

Byrom, "Miscellaneous Biomaterials," in *Biomaterials* (D. Byrom, ed.) pp. 333-359 MacMillan Publishers: London, 1991.

Conti, et al., "Use of polylactic acid for the preparation of microparticulate drug delivery systems", *J. Microencapsulation*, 9:153-166 (1992).

Cookson, "It grows on trees", *Financial Times*, p. 6 (Aug. 12, 1992).

Dayton, et al., "Use of an absorbable mesh to repair contaminated abdominal-wall defects", *Arch Surg.*, 121:954-960 (1986).

De Groot, "Meniscal tissue regeneration in porous 50/50 copoly(L-lactide/epsilon-caprolactone) implants", *Biomaterials*, 18(8):613-22 (1997).

De Smet, et al., "Characterization of intracellular inclusions formed by *Pseudomonas oleovorans* during growth on octane", *J. Bacteriol.*, 154:870-78 (1983).

Dubois, et al., "Macromolecular Engineering of Polylactones and Polylactides. 12. Study of the Depolymerization Reactions of Poly (-caprolactone) with Functional Aluminum Alkoxide End Groups", *Macromolecules*, 26:4407-12 (1993).

Duvernoy, et al. "A biodegradable patch used as a pericardial substitute after cardiac surgery: 6- and 24-month evaluation with CT", *Thorac. Cardiovasc. Surg.*, 43(5):271-74 (1995).

Encyclopedic Handbook of Biomaterials and Bioengineering, Part A: Materials, vol. 1 eds. Wise, et al.; Marcel Dekker, Inc., New York, 1995.

Freed, et al., "Biodegradable polymer scaffolds for tissue engineering", *Biotechnology*, 12:689-693 (1994).

Fukuzaki, et al., "Direct copolymerization of L-lactic acid with ÿ-butyrolactone in the absence of catalysts", *Die Madromoleculare Chemie*, 190:1553-59 (1989).

Gagnon, et al., "Chemical modification of bacterial elastomers: 1. Peroxide crosslinking", *Polymer*, 35:4358-67 (1994).

Gagnon, et al., "A thermoplastic elastomer produced by the bacterium *Pseudomonas oleovarans*", *Rubber World*, 207:32-38 (1992).

Gerngross & Martin, "Enzyme-catalyzed synthesis of poly[(R)-(-)-3-hydroxybutyrate]: formation of macroscopic granules in vitro," *Proc. Natl. Acad. Sci. USA*, 92:6279-83 (1995).

Gross, et al., "Polymerization of β-Monosubstituted-β-propiolactones Using Trialkylaluminum-Water Catalytic Systems and Polymer Characterization", *Macromolecules*, 21:2657-68 (1988).

Hocking & Marchessault, "Biopolyesters" in *Chemistry and Technology of Biodegradable Polymers*, (G.J.L. Griffin, ed.), pp. 48-96, Chapman and Hall: London, 1994.

Hocking & Marchessault, "Syndiotactic poly[(R,S)-β-hydroxybutyrate] isolated from methyaluminoxane-catalyzed polymerization", *Polym. Bull.*, 30:163-70 (1993).

Holmes, "Biologically Produced (R)-3-hydroxyalkanoate Polymers and Copolymers", in *Developments in Crystalline Polymers* (Bassett, ed.), pp. 1-65, Elsevier: London, 1988.

Hori, et al., "Chemical synthesis of high molecular weight poly(3-hydroxybutyrate-co-4-hydroxybutyrate)", *Polymer*, 36:4703-05 (1995).

Hori, et al., "Ring-Opening Polymerization of Optically Active β-Butyrolactone Using Distannoxane Catalysts: Synthesis of High Molecular Wright Poly(3-hydroxybutyrate)", *Macromolecules*, 26:5533-34 (1993).

Hori, et al., "Ring-Opening Copolymerization of Optically Active β-Butyrolactone with Several Lactones Catalyzed by Distannoxane Complexes: Synthesis of New Biodegradable Polyesters", *Macromolecules*, 26:4388-90 (1993).

Horsch, "Inheritance of functional foreign genes in plants", *Science*, 223:496-498 (1984).

Huijberts, et al., "*Pseudomonas putida* KT2442 cultivated on glucose accumulates poly(3-hydroxyalkanoates) consisting of saturated and unsaturated monomers", *Appl Environ Microbiol.*, 58(2):536-44 (1992).

Hutmacher, et al., "A review of material properties of biodegradable and bioresorbable polymers and devices for GTR and GBR applications," *Int. J. Oral Maxillofac. Implants*, 11(5):667-78 (1996).

Keeler, "Don't Let Food Go To Waste—Make Plastic Out of It", *R&D Magazine*, pp. 52-57 (1991).

Keeler, "Plastics Grown in Bacteria Inch Toward the Market", *R&D Magazine*, pp. 46-52 (1991).

Kemnitzer, et al., "Preparation of predominantly Syndiotactic Poly(β-hydroxybutyrate) by the Tributylin Methoxide Catalyzed Ring-Opening Polymerization of racemic β-Butyrolactone", *Macromolecules*, 26:1221-29 (1993).

Kim and Mooney, "Engineering smooth muscle tissue with a predefined structure", *J. Biomed. Mat. Res.*, 41(2):322-332 (1998).

Kishida, et al., "Formulation-assisted biodegradable polymer matrices", *Chemical and Pharmaceutical Bulletin*, 37:1954-56 (1989).

Klinge, et al., "Functional assessment and tissue response of short- and long-term absorbable surgical meshes", *Biomaterials*, 22:1415-1424 (2001).

Koosha, "Preparation and characterization of biodegradable polymeric drug carriers", Ph.D. Dissertation, 1989, Univ. Nottingham, UK., *Diss. Abstr. Int.*, B 51:1206 (1990).

Koosha, et al., "Polyhydroxybutyrate as a drug carrier", *Crit. Rev. Ther. Drug Carrier Syst.*, 6(2):117-30 (1989).

Korte & Gelt, "Hochdruckreaktionen. II. Die Polymerisation Von ÿ butyrolacton und ÿ-valerolactam bei hohen drücken", *Polymer Lett.*, 4:685-89 (1966).

Kusaka, et al., "Microbial synthesis and Physical Properties of ultra-high-molecular-weight poly[(R)-3-hydroxybutyrate]", *Pure Appl. Chem.*, A35:319-35 (1998).

Lafferty, et al., "Microbial Production of Poly-b-hydroxybutyric acid", in *Biotechnology* (Rehm & Reed, Eds.), pp. 135-176, Verlagsgesellschaft: Weinheim, 1988.

Lamba, et al., "Degradation of polyurethanes", in *Polyurethanes in Biomedical Applications* (CRC Press:Boca Raton, Florida, 1998).

Le Borgne, et al., "Stereoelective polymerization of β-butyrolactone", *Polymer*, 30:2312-19 (1989).

Lee, et al., "Copolymerization of ÿ-butyrolactone and β-butyrolactone", *Macromol. Chem. Phys.*, 198:1109-20(1997).

Lemoigne & Roukhelman, "Fermetation β-Hydroxybutyrique Caracterisation et Evolution Des Produits de Deshydration et de Polymerisation de L'acide β-Dehydroxybutyrique", *Annales des fermentations*, 5:527-36 (1925).

Lloyd, et al., "Transformation of *Arabidopsis thalania* with *Agrobacterium tumefaciens*", *Science*, 234: 464-66 (1986).

Madison & Huisman, "Metabolic engineering of poly(3-hydroxyalkanoates): from DNA to plastic", *Microbiol. Molec. Biol. Rev.*, 63:21-53 (1999).

Malm, et al., "Enlargement of the right ventricular outflow tract and the pulmonary artery with a new biodegradable patch in transannular position", *Eur. Surg. Res.*, 26(5):298-308 (1994).

Malm, et al., "A new biodegradable patch for closure of atrial septal defect. An experimental study", *Scand. J. Thorac. Cardiovasc. Surg.*, 26(1):9-14 (1992).

Malm, et al., "Prevention of postoperative pericardial adhesions by closure of the pericardium with absorbable polymer patches. An experimental study", *J. Thorac. Cardiovasc. Surg.*, 104(3):600-07 (1992).

Mathiowitz & Langer, "Polyanhydride microspheres as drug delivery systems", in *Microcapsules Nanopart. Med. Pharm.* (Donbrow, ed.), pp. 99-123 (CRC:Boca Raton, Florida, 1992).

Maysinger, et al., "Microencapsulation and the Grafting of Genetically Transformed Cells as Therapeutic Strategies to rescue Degenerating Neurons of the CNS", *Reviews in the Neurosciences*, 6:15-33 (1995).

McMillin, et al., "Elastomers for Biomedical Applications," *Rubber Chemistry and Technology*, 67:417-446 (1994).

McWiliams, "Plastics as high as an elephant's eye?" *Business Week*, pp. 110-111 (Aug. 19, 1991).

Müller, et al., "Poly(hydroxyalkanoates): A Fifth Class of Physiologically Important Organic Biopolymers", *Angew. Chem. Int. Ed. Engl.*, 32: 477-502 (1993).

Nakamura, et al., "Microbial synthesis and characterization of poly(3-hydroxybutyrate-*co*-4-hydroxybutyrate)", *Macromol.*, 25:4237-41 (1992).

Nobes, et al., "Polyhydroxyalkanoates: Materials for delivery systems", *Drug Del.*, 5:167-77 (1998).

Ogawa, et al., "A New Technique to Efficiently Entrap Leuprolide Acetate into Microcapsules of Poly Lactic Acid or Copoly(Lactic/Glycolic) Acid", *Chem. Pharm. Bull.*, 36:1095-103 (1988).

Otera, et al., "Novel template effects of distannoxane catalysts in highly efficient transesterification and esterification", *J. Org. Chem.*, 56:5307-11 (1991).

Otera, et al., "Distannoxane-catalysed transesterification of 1,*n*-Dioldiacetates. Selective transformation of either of chemically equivalent functional groups", *J. Chem. Soc. Chem. Commun.*, 1742-43 (1991).

Otera, et al., "Distannoxane as reverse micelle-type catalyst: novel solvent effect on reaction rate of transesterification", *J. Org. Chem.*, 54:4013-14 (1989).

Otera, et al., "Novel distannoxane-catalyzed transesterification and a new entry to ÿ,ÿ-unsaturated carboxylic acids", *Tetrahedron Lett.*, 27:2383-86 (1986).

Peoples, et al., "Polyhydroxybutyrate (PHB): A Model System for Biopolymer Engineering: II", in *Novel Biodegradable Microbial Polymers* (Dawes, ed.) pp. 191-202, Kluwer Academic Publishers:Netherlands (1990).

Peoples, et al., "Poly-β-hydroxybutyrate Biosynthesis in *Alcaligenes eutrophus* H16", *J. Biol. Chem*, 264(26):15293-97 (1989).

Perrin & English, "Polycaprolactone", in *Handbook of Biodegradable Polymers* (Domb, et al., eds.) pp. 63-77 (Harwood, Amsterdam, 1997).

Pinto, "Hydrogen Peroxide as depyrogenation agent for medical devices components", *Revista De Saude Publica*, 29(1):75-79 (1995).

Poirier, et al., "Progress Toward Biologically Produced Biodegradable thermoplastics", *Adv. Mater.*, 5(1):30-37 (1993).

Poirier, "Perspectives on the production of polyhydroxyalkanoates in plants", *FEMS Microbiology Reviews*, 103:237-46 (1992).

Pool, "In Search of the Plastic Potato", *Science*, 245: 1187-89 (1989).

Pouton & Akhtar, "Biosynthetic polyhydroxyalkanoates and their potential in drug delivery", *Adv. Drug Delivery Rev.*, 18:133-62 (1996).

Rivard, et al., "Fibroblast seeding and culture in biodegradable porous substrates", *J. Appl. Biomater.*, 6(1):65-68 (1995).

Saito, et al., "Microbial synthesis and properties of poly(3-hydroxybutyrate-co-4-hydroxybutyrate) in *Comamonas acidovorans*", *Int. J. Biol. Macromol.*, 16(2):99-104 (1994).

Schwartz & Goodman, *Plastic Materials and Processes*, (Van Nostrand Reinhold Company:New York, 1982).

Shin'Oka & Mayer, "New frontiers in tissue engineering: tissue engineered heart valves", in *Synthetic Biodegradable Polymer Scaffolds* (Atala & Mooney, eds.) pp. 187-198 Birkhäuser Boston, 1997.

Sim, et al., "PHA synthase activity controls the molecular weight and polydispersity of polyhydroxybutyrate in vivo", *Nat. Biotechnol.*, 15(1):63-67 (1997).

Stanton & Gagné, "The remarkable catalytic activity of alkali-metal alkoxide clusters in the ester interchange reaction", *J. Am. Chem. Soc.*, 119:5075-76 (1997).

Steinbüchel & Valentin, "Diversity of bacterial polyhydroxyalkanoic acids," *FEMS Microbiol. Lett.*, 128:219-28 (1995).

Steinbüchel & Wiese, "*A Pseudomonas* strain accumulating polyesters of 3-hydroxybutyric acid and medium-chain-length 3-hydroxyalkanoic acids", *Appl. Microbiol. Biotechnol.*, 37:691-97 (1992).

Steinbüchel, "Molecular basis for biosynthesis and accumulation of polyhydroxyalkanoic acids in bacteria", *FEMS Microbiol. Rev.*, 103:217-230 (1992).

Steinbüchel, "Polyhydroxyalkanoic Acids", in *Biomaterials* (D. Byrom ed.), pp. 123-213, MacMillan Publishers: London, 1991.

Tanahashi, et al., "Thermal Properties and Stereoregularity of Poly(3-hydroxybutyrate) Prepared from optically Active β-Butyrolactone with a Zinc-Based Catalyst", *Macromolecules*, 24:5732-33 (1991).

Valentin, et al., "Identification of 5-hydroxyhexanoic acid, 4-hydroxyaheptanoic acid and 4-hydroxyoctanoic acid as new constituents of bacterial polyhydroxyalkanoic acids", *Appl. Microbiol. Biotechnol.*, 46:261-67 (1996).

Valentin, et al., "Identification of 4-hydroxyvaleric acid as a constituent of biosynthetic polyhydroxyalkanoic acids from bacteria", *Appl. Microbiol. Biotechnol.*, 36:507-514 (1994).

Valentin, et al., "Identification of 4-hydroxyhexanoic acid as a new constituent of biosynthetic polyhydroxyalkanoic acids from bacteria", *Appl. Microbiol. Biotechnol.*, 40:710-16 (1994).

Wallen & Rohwedder, "Poly-β-hydroxyalakaonate from Activated Sludge", *Environ. Sci. Technol.*, 8:576-79 (1974).

Williams & Peoples, "Biodegradable plastics from plants", *Chemtech*, 26:38-44 (1996).

Williams & Peoples, "Making plastics green", *Chem. Br.*, 33:29-32 (1997).

Williams, et al., "Application of PHAs in Medicine and Pharmacy", *Polyesters*, III, 4:91-127 (2002).

Williams, et al., "PHA applications: addressing the price performance issue. I. Tissue engineering", *Int. J. Biol. Macromol.*, 25(1-3): 111-121 (1999).

Wong & Mooney, "Synthesis and properties of biodegradable polymers used as synthetic matrices for tissue engineering", in *Synthetic Biodegradable Polymer Scaffolds* (Atala, et al., eds.) pp. 51-82 (Birkhäuser: Boston, 1997).

Yagmurlu, et al., "Sulbactam-cefoperazone polyhydroxybutyrate-co-hydroxyvalerate (PHBV) local antibiotic delivery system: in vivo effectiveness and biocompatibility in the treatment of implant-related experimental osteomyelitis", *J Biomed Mater Res.*, 46(4):494-503 (1999).

Xie, et al., "Ring-opening Polymerization of β-Butyrolactone by Thermophilic Lipases", *Macromolecules*, 30:6997-98 (1997).

Anderson, et al., "Occurence, Metabolism, metabolic Role, and Industrial Uses of bacterial Polyhydroxyalkanoates," *Microbiological Reviews*, pp. 450-472 (1990).

Bailey, "Free radical ring-opening polymerization," *J. Polym. Preprints*, 25:210-11 (1984).

Boeree, et al., "Development of a degradable composite for orthopaedic use: mechanical evaluation of an hydroxyapatite-polyhydroxybutyrate composite material", *Biomaterials*. 14(10):793-6 (1993).

Braunegg, et al., "Polyhydroxyalkanoates, biopolyesters from renewable resources: physiological and engineering aspects," *J. Biotech.*, 65: 127-161 (1998).

Byrom, "Miscellaneous Biomaterials," in *Biomaterials* (D. Byrom, ed.) pp. 333-359 MacMillan Publishers: London, 991.

Conti, et al., "Use of polylactic acid for the preparation of microparticulate drug delivery systems," *J. Microencapsulation*, 9:153-166 (1992).

Cookson, "It grows on trees," *Financial Times*, p. 6 (Aug. 12, 1992).

De Groot, "Meniscal tissue regeneration in porous 50/50 copoly(L-lactide/epsilon-caprolactone) implants," *Biomaterials*, 18(8):613-22 (1997).

De Smet, et al., "Characterization of intracellular inclusions formed by *Pseudomonas oleovorans* during growth on octane," *J. Bacteriol.*, 154:870-78 (1983).

Dubois, et al., "Macromolecular Engineering of Polylactones and Polylactides. 12. Study of the Depolymerization Reactions of Poly(-caprolactone) with Functional Aluminum Alkoxide End Groups," *Macromolecules*, 26:4407-12 (1993).

Duvernoy, et al. "A biodegradable patch used as a pericardial substitute after cardiac surgery: 6- and 24-month evaluation with CT," *Thorac. Cardiovasc. Surg.*, 43(5):271-74 (1995).

Fukuzaki, et al., "Direct copolymerization of L-lactic acid with ÿ-butyrolactone in the absence of catalysts," *Die Madromoleculare Chemie*, 190:1553-59 (1989).

Gagnon, et al., "A thermoplastic elastomer produced by the bacterium *Pseudomonas oleovarans*, " *Rubber World*, 207:32-38 (1992).

Gagnon, et al., "Chemical modification of bacterial elastomers: 1. Peroxide crosslinking," *Polymer*, 35:4358-67 (1994).

Gross, et al., "Polymerization of β-Monosubstituted-β-propiolactones Using Trialkylaluminum-Water Catalytic Systems and Polymer Characterization," *Macromolecules*, 21:2657-68 (1988).

Hocking & Marchessault, "Syndiotactic poly[(R,S)-β-hydroxybutyrate] isolated from methyaluminoxane-catalyzed polymerization," *Polym. Bull.*, 30:163-70 (1993).

Holmes, "Biologically Produced (*R*)-3-hydroxyalkanoate Polymers and Copolymers," in *Developments in Crystalline Polymers* (Bassett, ed.), pp. 1-65, Elsevier: London, 1988.

Hori, et al., "Chemical synthesis of high molecular weight poly(3-hydroxybutyrate-*co*-4-hydroxybutyrate)," *Polymer*, 36:4703-05 (1995).

Hori, et al., "Ring-Opening Polymerization of Optically Active β-Butyrolactone Using Distannoxane Catalysts: Synthesis of High Molecular Wright Poly(3-hydroxybutyrate)," *Macromolecules*, 26:5533-34 (1993).

Hori, et al., "Ring-Opening Copolymerization of Optically Active β-Butyrolactone with Several Lactones Catalyzed by Distannoxane Complexes: Synthesis of New Biodegradable Polyesters," *Macromolecules*, 26:4388-90 (1993).

Keeler, "Don't Let Food Go To Waste—Make Plastic Out of It," *R&D Magazine*, pp. 52-57 (1991).

Keeler, "Plastics Grown in Bacteria Inch Toward the Market," *R&D Magazine*, pp. 46-52 (1991).

Kemnitzer, et al., "Preparation of predominantly Syndiotactic Poly(β-hydroxybutyrate) by the Tributylin Methoxide Catalyzed Ring-Opening Polymerization of racemic β-Butyrolactone," *Macromolecules*, 26:1221-29 (1993).

Kishida, et al., "Formulation-assisted biodegradable polymer matrices," *Chemical and Pharmaceutical Bulletin*, 37:1954-56 (1989).

Koosha, "Preparation and characterization of biodegradable polymeric drug carriers," Ph.D. Dissertation, 1989, Univ. Nottingham, UK., *Diss. Abstr. Int.*, B 51:1206 (1990).

Koosha, et al., "Polyhydroxybutyrate as a drug carrier," *Crit. Rev. Ther. Drug Carrier Syst.*, 6(2):117-30 (1989).

Korte & Gelt, "Hochdruckreaktionen. II. Die Polymerisation Von ÿ butyrolacton und ÿ-valerolactam bei hohen drücken," *Polymer Lett.*, 4:685-89 (1966).

Kusaka, et al., "Microbial synthesis and Physical Properties of ultra-high-molecular-weight poly[(R)-3-hydroxybutyrate]," *Pure Appl. Chem.*, A35:319-35 (1998).

Lafferty, et al., "Microbial Production of Poly-b-hydroxybutyric acid" in *Biotechnology* (Rehm & Reed, Eds.), pp. 135-76, Verlagsgesellschaft:Weiheim, 1988.

Lamba, et al., "Degradation of polyurethanes," in *Polyurethanes in Biomedical Applications* (CRC Press:Boca Raton, Florida, 1998).

Le Borgne, et al., "Stereoelective polymerization of β-butyrolactone," *Polymer*, 30:2312-19 (1989).

Lee, et al., "Copolymerization of ÿ-butyrolactone and β-butyrolactone," *Macromol. Chem. Phys.*, 198:1109-20 (1997).

Lemoigne & Roukhelman, "Fermetation β-Hydroxybutyrique Caracterisation et Evolution Des Produits de Deshydration et de Polymerisation de L'acide β-Dehydroxybutyrique," *Annales des fermentations*, 5:527-36 (1925).

Lloyd, et al., "Transformation of *Arabidopsis thalania* with *Agrobacterium tumefaciens*," *Scienc*, 234: 464-66 (1986).

Madison & Huisman, "Metabolic engineering of poly(3-hydroxyalkanoates): from DNA to plastic," *Microbiol. Molec. Biol. Rev.*, 63:21-53 (1999).

Malm, et al., "Enlargement of the right ventricular outflow tract and the pulmonary artery with a new biodegradable patch in transannular position," *Eur. Surg. Res.*, 26(5):298-308 (1994).

Malm, et al., "A new biodegradable patch for closure of atrial septal defect. An experimental study," *Scand. J. Thorac. Cardiovasc. Surg.*, 26(1):9-14 (1992).

Malm, et al., "Prevention of postoperative pericardial adhesions by closure of the pericardium with absorbable polymer patches. An experimental study," *J. Thorac. Cardiovasc. Surg.*, 104(3):600-07 (1992).

Mathiowitz & Langer, "Polyanhydride microspheres as drug delivery systems" in *Microcapsules Nanopart. Med. Pharm.* (Donbrow, ed.), pp. 99-123 (CRC:Boca Raton, Florida, 1992).

Maysinger, et al., "Microencapsulation and the Grafting of Genetically Transformed Cells as Therapeutic Strategies to rescue Degenerating Neurons of the CNS," *Reviews in the Neurosciences*, 6:15-33 (1995).

Müller, et al., "Poly(hydroxyalkanoates): A Fifth Class of Physiologically Important Organic Biopolymers," *Angew. Chem. Int. Ed. Engl.*, 32: 477-502 (1993).

Nakamura, et al., "Microbial synthesis and characterization of poly(3-hydroxybutyrate-*co*-4-hydroxybutyrate)," *Macromol.*, 25:4237-41 (1992).

Nobes, et al., "Polyhydroxyalkanoates: Materials for delivery systems," *Drug Del.*, 5:167-77 (1998).

Ogawa, et al., "A New Technique to Efficiently Entrap Leuprolide Acetate into Microcapsules of Poly Lactic Acid or Copoly(Lactic(Glycolic) Acid," *Chem. Pharm. Bull.*, 36:1095-103 (1988).

Otera, et al., "Novel template effects of distannoxane catalysts in highly efficient transesterification and esterification," *J. Org. Chem.*, 56:5307-11 (1991).

Otera, et al., "Distannoxane-catalysed transesterification of 1, *n*-Dioldiacetates. Selective transformation of either of chemically equivalent functional groups," *J. Chem. Soc. Chem. Commun.*, 1742-43 (1991).

Otera, et al., "Distannoxane as reverse micelle-type catalyst: novel solvent effect on reaction rate of transesterification," *J. Org. Chem.*, 54:4013-14 (1989).

Otera, et al., "Novel distannoxane-catalyzed transesterification and a new entry to ÿ,ÿ-unsaturated carboxylic acids," *Tetrahedron Lett.*, 27:2383-86 (1986).

Peoples, et al., "Polyhydroxybutyrate (PHB): A Model System for Biopolymer Engineering: II," in *Novel Biodegradable Microbial Polymers* (Dawes, ed.) pp. 191-202, Kluwer Academic Publishers:Netherlands (1990).

Peoples, et al., "Poly-β-hydroxybutyrate Biosynthesis in *Alcaligenes eutrophus* H16," *J. Biol. Chem*, 264(26):15293-97 (1989).
Perrin & English, "Polycaprolactone," in *Handbook of Biodegradable Polymers* (Domb, et al., eds.) pp. 63-77 (Harwood, Amsterdam, 1997).
Poirier, et al., "Progress Toward Biologically Produced Biodegradable thermoplastics," *Adv. Mater.*, 5(1):30-37 (1993).
Poirier, "Perspectives on the production of polyhydroxyalkanoates in plants," *FEMS Microbiology Reviews*, 103:237-46 (1992).
Pool, "In Search of the Plastic Potato," *Science*, 245: 1187-89 (1989).
Pouton & Akhtar, "Biosynthetic polyhydroxyalkanoates and their potential in drug delivery," *Adv. Drug Delivery Rev.*, 18:133-62 (1996).
Rivard, et al., "Fibroblast seeding and culture in biodegradable porous substrates," *J. Appl. Biomater.*, 6(1):65-68 (1995).
Saito, et al., "Microbial synthesis and properties of poly(3-hydroxybutyrate-co-4-hydroxybutyrate) in *Comamonas acidovorans*," *Int. J. Biol. Macromol.*, 16(2):99-104 (1994).
Shin'Oka & Mayer, "New frontiers in tissue engineering: tissue engineered heart valves" in *Synthetic Biodegradable Polymer Scaffolds* (Atala & Mooney, eds.) pp. 187-198 Birkhäuser Boston, 1997.
Sim, et al., "PHA synthase activity controls the molecular weight and polydispersity of polyhydroxybutyrate in vivo," *Nat. Biotechnol.*, 15(1):63-67 (1997).
Stanton & Gagné, "The remarkable catalytic activity of alkali-metal alkoxide clusters in the ester interchange reaction," *J. Am. Chem. Soc.*, 119:5075-76 (1997).
Steinbüchel & Wiese, "*A Pseudomonas* strain accumulating polyesters of 3-hydroxybutyric acid and medium-chain-length 3-hydroxyalkanoic acids," *Appl. Microbiol. Biotechnol.*, 37:691-97 (1992).
Steinbüchel, "Molecular basis for biosynthesis and accumulation polyhydroxyalkanoic acids in bacteria," *FEMS Microbiol. Rev.*, 103:217-230 (1992).
Steinbüchel, "Polyhydroxyalkanoic Acids," in *Biomaterials* (D. Byrom ed.), pp. 123-213, MacMillan Publishers: London, 1991.
Tanahashi, et al., "Thermal Properties and Stereoregularity of Poly(3-hydroxybutyrate) Prepared from optically Active β-Butyrolactone with a Zinc-Based Catalyst," *Macromolecules*, 24:5732-33 (1991).
Valentin, et al., "Identification of 5-hydroxyhexanoic acid, 4-hydroxyaheptanoic acid and 4-hydroxyoctanoic acid as new constituents of bacterial polyhydroxyalkanoic acids," *Appl. Microbiol. Biotechnol.*, 46:261-67 (1996).
Valentin, et al., "Identification of 4-hydroxyvaleric acid as a constituent of biosynthetic polyhydroxyalkanoic acids from bacteria," *Appl. Microbiol. Biotechnol.*, 36:507-514 (1994).
Valentin, et al., "Identification of 4-hydroxyhexanoic acid as a new constituent of biosynthetic polyhydroxyalkanoic acids from bacteria," *Appl. Microbiol. Biotechnol.*, 40:710-16 (1994).
Wallen & Rohwedder, "Poly-β-hydroxyalakaonate from Activated Sludge," *Environ. Sci. Technol.*, 8:576-79 (1974).
Williams & Peoples, "Biodegradable plastics from plants," *Chemtech*, 26:38-44 (1996).
Williams & Peoples, "Making plastics green," *Chem. Br.*, 33:29-32 (1997).
Williams, et al., "PHA applications: addressing the price performance issue. I. Tissue engineering," *Int. J. Biol. Macromol.*, 25(1-3): 111-121 (1999).
Wong & Mooney, "Synthesis and properties of biodegradable polymers used as synthetic matrices for tissue engineering," in *Synthetic Biodegradable Polymer Scaffolds* (Atala, et al., eds.) pp. 51-82 (Birkhäuser: Boston, 1997).
Xie, et al., "Ring-opening Polymerization of β-Butyrolactone by Thermophilic Lipases," *Macromolecules*, 30:6997-98 (1997).
Kassab, "Rifampicin carrying polyhydroxybutyrate microspheres as a potential chemoembolization agent", Journal of Biomaterials Science, Polymer Edition, 8(12):947-961 (1997).
Abate, et al., "Separation and structural characterizations of cyclic and open chain oligomers produced in the partial pyrolysis of microbial poly(hydroxyutyrates)", *Macromolecules*, 28(23):7911-1916 (1995).

Addolorato, et al., "Maintaining abstinence from alcohol with gamma-hydroxybutyric acid", *The Lancet*, 351:38 (1998).
Andriamampandry, et al., "Cloning of a rat brain succinic semialdehyde reductase involved in the synthesis of the neuromodulator γ-hydroxybutyrate", *Biochem. J.*, 334:43-50 (1998).
Bandiera, et al., "Effect of sodium sulfonate groups on the ionic conductivity of a copolyester of thiodipropionic acid", *Eur. Pol. J.*, 33:1679-1683 (1997).
Behrend, "PHB as a bioresorbable material for intravascular stents," *American J. Cardiol.* p. 45, TCT Abstracts (Oct. 1998).
Berde, et al., "Sustained release of dibucaine from a biodegradable polymer matrix: A potential method for prolooged neural blockade", Abstracts of Scientific Papers, 1990 Annual Meeting, Ameri. Soc. Anesthesiologists, 73(3A):A776, (Sep. 1990).
Blight, "Miracles and molecules—progress in spinal cord repair.," *Nat. Neurosci* 5:1051-4 (2002).
Brandl, et al., "*Pseudomonas oleovorans* as a source of poly(b-hydroxyalkanoates for potential applications as biodegradable polyesters", *Appl. Environ. Microbiol.*, 54:1977-1982 (1988).
Breuer, et al., "Tissue Engineering Lamb Heart Valve Leaflets," *Biotechnology & Bioengineering* 50:562-67 (1996).
Campbell & Bailey, "Mechanical properties of suture materials in vitro and after in vivo implantation in horses," *Vet. Surg.* 21(5):355-61 (1992).
Chu, et al., *Wound Closure Biomaterials and Devices* CRC Press:Boca Raton, 1996.
Colombo, et al., "Involvement of GABA(A) and GABA(B) receptors in the mediation of discriminative stimulus effects of gamma-hydroxybutyric acid", *Physiology & Behavior*, 64:293-302 (1998).
Cuebas, et al., "Mitochondrial metabolism of 3-mercaptopropionic acid. Chemical synthesis of 3-mercaptopropionyl coenzyme A and some of its S-acyl derivatives", *J. Biol. Chem.*, 260:7330-7336 (1985).
Damien & Parsons, "Bone graft and bone graft substitutes: a review of current technology and applications," *J. Appl. Biomater.* 2(3):187-208 (1991).
De Koning, et al., "A biodegradable rubber by crosslinking poly(hydroxyalkanoate) from *Pseudomonas oleovorans*", *Polymer*, 35:2090-97 (1994).
Domb, et al., *Handbook of Biodegradable Polymers* (Harwood Academic Publishers:Amsterdam, The Netherlands, 1997).
Entholzner, et al., "EEG changes during sedation with gamma-hydroxybutyric acid", *Anaesthesist*, 44:345-350 (1995).
Fraser, et al., "Controlled release of a GnRH agonist from a polyhydroxybutyric acid implant-reversible suppression of the menstrual cycle in the macaque," *Acta Endocrinol* 121:841-848 (1989).
Füchtenbusch, et al., "Biosynthesis of novel copolyesters containing 3-hydroxypivalic acid by *Rhodoccus ruber* NCIMB 40126 and related bacteria", *FEMS Microbiol. Lett.*, 159:85-92 (1998).
Gabbay, et al., "New outlook on pericardial substitution after open heart operations", *Ann. Thorac. Surg.*, 48(6):803-12 (1989).
Gagnon, et al., "Chemical modification of bacterial elastomers: 2. Sulfur vulvanization", *Polymer*, 35:4368-75 (1994).
Gerra, et al., "Flumazenil effects on growth hormone response to gamma-hydroxybutyric acid", *International Clinical Psychopharmacology*, 9:211-215 (1994).
Griebel, et al., "Metabolism of poly-beta-hydroxybutyrate. I. Purification, composition, and properties of native poly-beta-hydroxybutyrate granules from *Bacillus megaterium*", *Biochemistry*, 7:3676-3681 (1968).
Gugala, et al., Regeneration of segmental diaphyseal defects in sheep tibiae using resorbable polymeric membranes: a preliminary study, *J. Orthop. Trauma.* 13(3):187-95 (1999).
Gürsel, et al., "In vivo application of biodegradable controlled antibiotic release systems for the treatment of implant-related osteomyelitis," *Biomaterials* 22: 73-80 (2001).
Hadlock, et al., "Ocular cell monolayers cultured on biodegradable substrates," *Tissue Eng.* 5(3):187-96 (1999).
Hazari, et al., "A new resorbable wrap-around implant as an alternative nerve repair technique", *J. Hand Surgery*, 24(3): 291-295 (1999).
Hazari, et al., "A resorbable nerve conduit as an alternative to nerve autograft in nerve gap repair", *Br J Plast Surg.*, 52(8):653-7 (1999).

Hein, et al., "Biosynthesis of poly(4-hydroxybutyric acid) by recombinant strains of *Escherichia coli,*" *FEMS Microbiol. Lett.* 153:411-18 (1997).

Heydorn, et al., "A new look at pericardial substitutes," *J. Thorac. Cardiovasc. Surg.* 94:291-96 (1987).

Hoke, "Mechanisms of Disease: what factors limit the success of peripheral nerve regeneration in humans?" *Nat. Clin. Pract. Neurol.* 448-454 (2006).

Holmes, et al., "Applications of PHB—a microbially produced biodegradable thermoplastic," *Phys Technol* 16:32-36 (1985).

Horowitz, et al., "Novel Thermal Route to an Amorphous, Film-Forming Polymer Latex", *Macromolecules,* 32:3347-3352 (1999).

Kameyama, et al., "Novel sequence-ordered polymers by transformation of polymer backbone: Quantitative and regioselective insertion of Thiranes into poly( S-aryl thioester)", *Macromol.,* 32:1407-1412 (1999).

Kassab, et al., "Embolization with polyhydroxybutyrate (PHB) microspheres: In vivo studies", *J. Bioact. Compat. Polym.,* 14:291-303 (1999).

Kaufman and Nelson, "An overview of gamma-hydroxybutyrate catabolism: the role of the cytosolic NADP(+)-dependent oxidoreductase EC 1.1.1.19 and of a mitochondrial hydroxyacid-oxoacid transhydrogenase in the initial, rate-limiting step in this pathway", *Neurochemical Research,* 16:965-974 (1991).

Kleinschmidt, et al., "Continuous sedation during spinal anaesthesia: gamma-hydroxybutyrate vs. propofol", *European Journal of Anaesthesiology,* 16:23-30 (1999).

Kleinschmidt, et al., "Total intravenous anaesthesia using propofol, gamma-hydroxybutyrate or midazolam in combination with sufentanil for patients undergoing coronary artery bypass surgery", *European Journal of Anesthesiology,* 14:590-599 (1997).

Korkusuz, et al., In vivo response to biodegradable controlled antibiotic release systems, *J. Biomed. Mater. Res.* 55: 217-228 (2001).

Korsatko, et al., "The influence of the molecular weight of poly-D(-)-3-hydroxybutyric acid on its use as a retard matrix for sustained drug release," *8th Europ. Congress of Biopharmaceutics and Pharmokinetics* 1:234-242(1987).

Lanza, et al., *Principles of Tissue Engineering* (Academic Press:Austin, 1997).

Lebedev and Yevstropov, "Thermoplastic properties of polylactones", *Makromol. Chem.,* 185:1235-1253 (1984).

Ljungberg, et al. "Neuronal survival using a resorbable synthetic conduit as an alternative to primary nerve repair", *Microsurgery,* 19(6):259-264 (1999).

Lütke-Eversloh et al., "Identification of a new class of biopolymer: Bacterial synthesis of a sulfur-containing polymer with thioester linkages", *Microbiology,* 147(1): 11-19 (2001).

Lütke-Eversloh et al., "List of submitted abstracts", *The 8th International Symposium on Biological Polyesters,* (2000).

Martin and Williams, "Medical application of poly-4-hydroxybutyrate: A strong flexible absorbable biomaterial", *Biochem. Eng. J.,* 16:97-105 (2003).

Modelli, et al., "Kinetics of aerobic polymer degradation in soil by means of the ASTM D 5988-96 standard method," *J Environ Polym Degr* 7:109-116 (1999).

Müh, et al., "PHA synthase from chromatium vinosum: cysteine 149 is involved in covalent catalysis", *Bioche.,* 38:826-837 (1999).

Nakamura et al., "Biosynthesis and characteristics of bacterial poly(3-hydroxybutyrate-co-3-hydroxypropionate)", *Macromol. Rep.,* A28, 15-24 (1991).

Nelson, et al., "The extraneural distribution of gamma-hydroxybutyrate", *J. Neurochem.,* 37:1345-1348 (1981).

Niklason, et al., "Functional arteries grown in vitro," *Science* 284(5413):489-93 (1999).

Pedrós-Alio et al., "The influence of poly-β-hydroxybutyrate accumulation on cell volume and buoyant density in *Alcaligenes eutrophus",* Arch. Microbiol. 143:178-184 (1985).

Rehm and Steinbüchel, "Biochemical and genetic analysis of PHA synthases and other proteins required for PHA synthesis", *Int. J. Biol. Macromol.* 25:3-19 (1999).

Renstad, et al., "The influence of processing induced differences in molecular structure on the biological and non-biological degradation of poly (3-hydroxybutyrate-co-3-hydroxyvalerate), P(3-HB-co-3-HV)," *Polymer Degradation and Stability* 63:201-211 (1999).

Reynolds, *Martindale: The Extra Pharmacopeia,* p. 1264, (Thirty First Edition, Royal Pharmaceutical Society, London, 1997).

Ropero-Miller & Goldberger, "Recreational drugs. Current trends in the 90s", *Clinics in Laboratory Medicine,* 18:727-746 (1998).

Sabbagh, et al., "3-Mercaptopropionic acid, a potent inhibitor of fatty acid oxidation in rat heart mitochondria", *J. Biol. Chem.* 260:7337-7342 (1985).

Scharf, et al., "Pharmacokinetics of gammahydroxybutyrate (GHB) in narcoleptic patents", *Sleep* 21:507-514 (1998).

Schlegel, et al., "Ein submersverfahren zur kultur wasserstoffoxydierender bakterien: Wachstumsphysiologische untersuchungen", *Arch. Mikrobiol.* 38:209-222 (1961).

Schmidt, et al "Neural tissue engineering: strategies for repair and regeneration," *Annu. Rev. Biomed. Eng.* 5:293-347 (2003).

Sendelbeck & Girdis, "Disposition of a 14C-labeled bioerodible polyorthoester and its hydrolysis products, 4-hydroxybutyrate and cis,trans-1,4-bis(hydroxymethyl)cyclohexane, in rats", *Drug Metabolism & Disposition* 13:291-295 (1985).

Shinoka, et al., "Creation of viable pulmonary artery autografts through tissue engineering," *J. Thorac. Cardiovasc. Surg.* 115(3):536-46 (1998).

Shinoka, et al., "Tissue engineering heart valves: valve leaflet replacement study in a lamb model" *Ann. Thorac. Surg.* 60(6 Suppl):S513-16 (1995).

Skrede et al, "Thia fatty acids, metabolism and metabolic effects" in *Biochim Biophys Acta* 1344:115-31(1997).

Snead, "The gamma-hydroxybutyrate model of absence seizures: correlation of regional brain levels of gamma-hydroxybutyric acid and gamma-butyrolactone with spike wave discharges", *Neuropharmacology* 30:161-167 (1991).

Song, et al., "Production of poly(4-hydroxybutyric acid) by fed-batch cultures of recombinant strains of *Escherichia coli", Biotechnol. Lett.* 21:193-197 (1999).

Speer & Warren, "Arthroscopic shoulder stabilization. A role for biodegradable materials," *Clin. Orthop.* (291):67-74 (1993).

Takagi et al., "Biosynthesis of polyhydroxyalkanoate with a thiophenoxy side group obtained from *Pseudomonas putida"*, *Macromolecules,* 32: 8315-8318 (1999).

Talja, et al., "Bioabsorbable and biodegradable stents in urology," *J. Endourol.* 11(6):391-97 (1997).

Tanaka, et al., "Clinical application of 4-hydroxybutyrate sodium and 4-butyrolactone in neuropsychiatric patients", *Folia Psychiatrica et Neurologica* 20:9-17 (1966).

Tanguay, et al., "Current status of biodegradable stents," *Cardiol. Clin.* 12(4):699-713 (1994).

Tsuruta, et al., *Biomedical Applications of Polymeric Materials* (CRC Press, Boca Raton, Florida, 1993).

Tunnicliff, "Sites of action of gamma-hydroxybutyrate (GHB)—a neuroactive drug with abuse potential", *Clinical Toxicology,* 35:581-590 (1997).

Türesin, et al., "Biodegradable polyhydroxyalkanoate implants for osteomyelitis therapy: in vitro antibiotic release," *J. Biomater. Sci. Polymer Edn.* 12: 195-207 (2001).

Turke, "Absorbable Biomaterial is suited for diverse applications" (Jun. 3, 2002). Retrieved on Dec. 17, 2004, from http://www.devicelink.com/mpmn/archive/01/10/009.html.

Unverdorben, et al., "Polyhydroxybutyrate (PHB) Biodegradable Stent-Experience in the Rabbit," *American J. Cardiol.* p. 46, TCT Abstracts (Oct. 1998).

Valentin, et al., "Production of poly(3-hydroxybutyrate-co-4-hydroxybutyrate) in recombinant *Escherichia coli* grown on glucose," *J. Biotechnol.* 58:33-38 (1997).

Von Schroeder, et al., "The use of polylactic acid matrix and periosteal grafts for the reconstruction of rabbit knee articular defects," *J. Biomed. Mater. Res.* 25(3):329-39 (1991).

Widmer & Mikos, "Fabrication of biodegradable polymer scaffolds for tissue engineering" in *Frontiers in Tissue Engineering* (Patrick, et al., Eds.) Ch. II.5, pp. 107-120 (Elsevier Science, New York, 1998).

Wodzinska, et al., "Polyhydroxybutyrate synthase: Evidence for covalent catalysis", *J. Am. Chem. Soc.* 118:6319-6320 (1996).

Worsey and Williams, "Metabolism of toluene and xylenes by *Pseudomonas putida* (*arvilla*) mt-2: evidence for a new function of the TOL plasmid" *J Bacteriol* 124:7-13 (1975).

Yamada, et al., "Development of a dural substitute from synthetic bioabsorbable polymers," *J. Neurosurg.* 86(6):1012-17 (1997).

Yiu, et al. "Glial inhibition of CNS axon regeneration," *Nat. Rev. Neurosci.* 7:617-627 (2006).

Zund, et al., "The in vitro construction of a tissue engineered bioprosthetic heart valve," *Eur. J. Cardiothorac. Surg.* 11(3):493-97 (1997).

Tepha announces submission of device master file to FDA (Jun. 3, 2002). Retrieved Dec. 17, 2004, from http://www.pressrelease.be/script_UK/newsdetail.asp?ndays=m&ID=695.

Tepha submits device master file to FDA—New Technology (Jul. 2, 2002). Retrieved on Dec. 17, 2004, from http://www.findarticles.com/p/articles/mi_mOPC/is_7_26/ai_89018276.

Valappil, et al., "Biomedical applications of polyhydroxyalkanoates, an overview of animal testing and in vivo responses", *Expert Rev. Med. Devices*, 3(6):853-868 (2006).

\* cited by examiner

METHOD OF MAKING A POLYHYDROXYALKANOATE FILAMENT

CROSS-REFERENCE TO RELATED APPLICATIONS

This application claims priority under 35 U.S.C. 119 to U.S. Ser. No. 60/598,296 entitled "Non-Curling Polyhydroxyalkanoate Sutures" by Said Rizk, filed on Aug. 3, 2004.

The U.S. government has certain rights to this invention by virtue of grants 70NANB2H3053 from the Department of Commerce, awarded on Nov. 1, 2002; and 1R43GM64863-01 and 2R44GM064863-02 from the National Institutes of Health awarded on May 10, 2002 and Mar. 10, 2004, respectively.

FIELD OF THE INVENTION

The present invention generally relates to fiber-based medical devices derived from poly-4-hydroxybutyrate and its copolymers.

BACKGROUND OF THE INVENTION

Poly-4-hydroxybutyrate (PHA4400) is a strong pliable thermoplastic that is produced by a fermentation process, as described in U.S. Pat. No. 6,548,569 to Williams et al. Despite its biosynthetic route, the structure of the polyester is relatively simple:

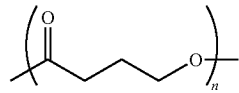

The polymer belongs to a larger class of materials called polyhydroxyalkanoates (PHAs) that are produced by numerous microorganisms. Steinbüchel, A., Polyhydroxyalkanoic acids, *Biomaterials*, 123-213 (1991); Steinbüchel A., et al., Diversity of Bacterial Polyhydroxyalkanoic Acids, *FEMS Microbial. Lett.* 128:219-228 (1995); and Doi, Y., *Microbial Polyesters* (1990). In nature these polyesters are produced as storage granules inside cells, and serve to regulate energy metabolism. They are also of commercial interest because of their thermoplastic properties, and relative ease of production. Several biosynthetic routes are currently known to produce PHA4400, as shown below:

Chemical synthesis of PHA4400 has been attempted, but it has been impossible to produce the polymer with a sufficiently high molecular weight necessary for most applications (Hori, Y., et al., *Polymer* 36:4703-4705 (1995)).

Tepha, Inc. (Cambridge, Mass.) produces PHA4400 and related copolymers for medical use, and has filed a Device Master File with the United States Food and Drug Administration (FDA) for PHA4400. Related copolymers include 4-hydroxybutyrate copolymerized with 3-hydroxybutyrate or glycolic acid, as described in U.S. Pat. No. 6,316,262 to Huisman et al., and U.S. Pat. No. 6,323,010 to Skraly et al. Tepha, Inc. has also filed a Device Master File with the United States FDA for copolymers containing 3-hydroxybutyrate and 4-hydroxybutyrate. Methods to control the molecular weight of PHA polymers have been disclosed in U.S. Pat. No. 5,811,272 to Snell et al., and methods to purify PHA polymers for medical use have been disclosed in U.S. Pat. No. 6,245,537 to Williams et al. PHAs with degradation rates in vivo of less than one year have been disclosed in U.S. Pat. No. 6,548,569 to Williams et al. and WO 99/32536 by Martin et al. The use of PHAs as tissue engineering scaffolds has also been disclosed in U.S. Pat. No. 6,514,515 to Williams, and other applications of PHAs have been reviewed in Williams, S. F., et al., *Polyesters, III,* 4:91-127 (2002).

In the practice of surgery there currently exists a need for absorbable fibers and surgical meshes with improved performance. For example, an absorbable hernia mesh with prolonged strength retention could have many advantages over the non-absorbable synthetic meshes currently used in hernia operations (Klinge, U., et al., *Biomaterials* 22:1415-1424 (2001)). Long-term implantation of these non-absorbable meshes is not considered ideal because they can lead to complications such as adhesions (fistula formation), pain, and restriction of physical capabilities (Klinge et al., 2001). If implanted into surgical sites that are contaminated or have the potential to become contaminated, 50-90% of these non-absorbable implants will need to be removed (Dayton et al., *Arch Surg.* 121:954-960 (1986)). These implants are also not ideal for use in pediatric patients where they could hinder growth (Klinge et al., 2001). To date, the use of absorbable synthetic surgical meshes in hernia repair has been found to almost invariably result in large incisional hernias that require revision operations because of the relatively short-term strength retention of these materials (Klinge et al., 2001). However, an absorbable hernia mesh with prolonged strength retention could solve this problem by providing a mechani-

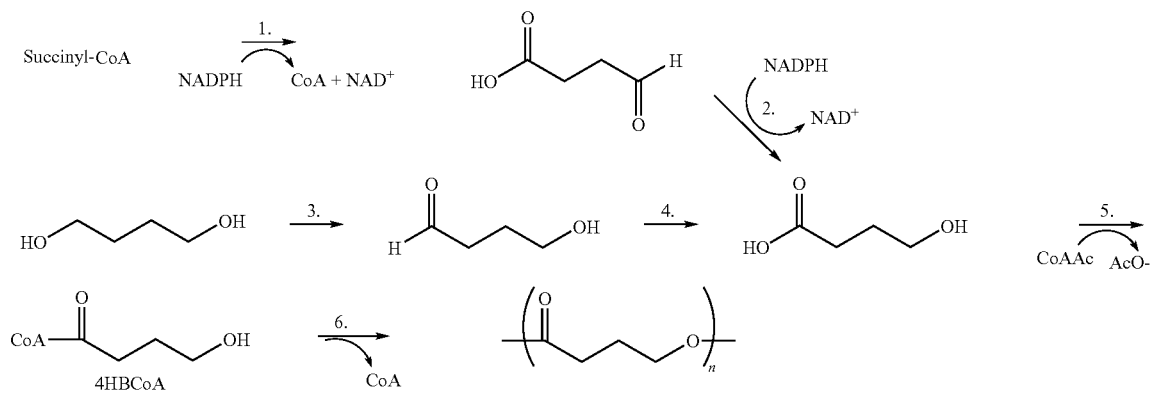

cally stable closure, which can reduce the incidence of adhesions and the risks of infection, and is suitable for use in pediatric patients.

There are also needs for improved meshes and patches for other procedures. In pericardial repair there exists a need for a surgical material that will prevent adhesions between the sternum and heart following open-heart surgery. There are also similar needs to prevent adhesions in spinal and gynecology procedures that could be addressed with improved surgical meshes and patches.

Biomaterial patches derived from animal and human tissue are currently used in cosmetic surgery, cardiovascular surgery, general surgery (including hernia repair), and in urology and gynecology procedures for the treatment of conditions that include vaginal prolapse and urinary incontinence. There is a growing concern about the use of animal and human derived biomaterials because of the risks associated with disease transmission. However, the synthetic absorbable meshes and patches that are currently available are limited, can be inflammatory, and do not provide prolonged strength retention. Thus there exists a need to provide new absorbable meshes for these procedures as well. Ideally, these products should have prolonged strength retention, induce minimal inflammatory responses that resolve, have good handling properties, provide mechanically stable reinforcement or closure, offer anti-adhesion properties (where necessary), minimize the risks of disease transmission, and after absorption leave a healthy natural tissue structure.

Thus, there is a need to develop absorbable fibers with prolonged strength retention that could be used as suturing materials or as surgical meshes.

In 1984, a division of Johnson and Johnson (Ethicon) first introduced a monofilament synthetic absorbable suture made from polydioxanone (sold as PDS™). This suture retains about 50% of its strength up to six weeks after implantation, and is completely absorbed in the body within six months. Davis and Geck subsequently introduced a monofilament suture based on a copolymer of glycolide and trimethylene carbonate (sold as Maxon™). This suture has similar strength retention to PDS™. Two other monofilament sutures were introduced more recently: one based on segmented copolymers of glycolide and caprolactone (sold as Monocryl™), and the other based on a terpolymer of glycolide, p-dioxanone, and trimethylene carbonate (sold as Biosyn™). Monocryl™ is reported to have a 20-30% breaking strength after 2-3 weeks, and is completely absorbed after 3-4 months. Biosyn™ has an absorption profile similar to Monocryl™. Despite continued innovation in the development of absorbable synthetic monofilament sutures there is still a need for a synthetic absorbable suture with extended strength retention for patients requiring long-term wound support. For example, a monofilament suture with 50% strength retention at 3-6 months (after implantation). There are also limited options for synthetic absorbable meshes with prolonged strength retention.

U.S. Pat. No. 6,548,569 to Williams et al. discloses that PHA4400 has a slower absorption rate in vivo than many materials used as absorbable sutures, and provides absorption data for unoriented PHA4400 films and porous samples. Methods to produce medical fibers and textiles from PHA4400 have previously been described by Martin et al. in WO 2004/101002. These methods were successful in producing fibers with prolonged strength retention. WO 2004/101002 discloses poly-4-hydroxybutyrate polymer that can be converted into fibers and devices with tensile strengths comparable to existing absorbable synthetic fibers such as PDS but with prolonged in vivo strength retention. It does not, however, disclose pliable, curl free fibers with increased tensile and knot tying properties as compared to currently available absorbable fibers such as PDS nor methods to produce these important properties.

It is therefore an object of this invention to provide new fibers, surgical meshes, and medical devices with improved handling properties and improved knot tying properties.

It is another object of this invention to provide methods for fabricating the articles and devices.

SUMMARY OF THE INVENTION

Absorbable devices such as suture fibers, braids, and surgical meshes with improved handling and methods for making these materials have been developed. These devices are preferably derived from biocompatible copolymers or homopolymers of 4-hydroxybutyrate. The devices provide a wider range of in vivo strength retention properties than are currently available, and improved handling properties. The devices are processed using a method that produces a non-curling fiber useful as a suture. Properties are enhanced by the addition of a relaxation step following orientation and an annealing step. The relaxation and annealing steps are carried out at a temperature from about 30 to about 150° C. and from about 35 to about 150° C., respectively. Introduction of an annealing process and relaxation step for the fiber further enhances the handling properties of the resulting fibers. The relaxation step allows the fiber to shrink and elongation is allowed to increase by as much as 25% followed by an annealing step either on or offline to further control and fine tune elongation, modulus and strength. The poly-4-hydroxybutyrate may additionally be combined with absorbable additives then processed through relaxation and/or annealing to further enhance fiber handling.

In a preferred method, polymer fibers with improved handling and less tendency to curl are prepared by extruding the fiber, as described above, and then using an aging step whereby partially drawn polymer filament is stored from 2 to 72 hours at temperatures between 0 and −80° C. before processing with hot stretching and annealing, as described above.

In yet another preferred method, polymer fibers with improved handling may be prepared by blending up to 15% by weight calcium stearate, calcium phosphate or similar materials into the polymer and then melt extruding the polymer into the desired filaments. The filaments may be further processed by hot stretching and annealing, as described above.

DETAILED DESCRIPTION OF THE INVENTION

I. Definitions

"Strength retention" as generally used herein means the amount of time that a material maintains a particular mechanical property following implantation into a human or animal. For example, if the tensile strength of an absorbable fiber decreased by half over three months when implanted into an animal, the fiber's strength retention at three months would be 50%.

"Biocompatible" as generally used herein means the biological response to the material or device being appropriate for the device's intended application in vivo. Any metabolites of these materials should also be biocompatible.

"Handling" as generally used herein means the ease with which a material or device can be manipulated, particularly by a medical practitioner.

"Curling" as generally used herein means the tendency of a fiber to curve or form coils during handling.

"Non-curling" as generally used herein means has a reduced tendency to curve or form coils during handling.

"Pliable fiber" as generally used herein refers to a fiber with reduced stiffness.

"Knot Conversion" as generally used herein refers to the ratio of knot strength to the tensile strength.

"Knot Security" as generally used herein refers to the knot resistance to become undone.

"Poly-4-hydroxybutyrate" as generally used herein means a homopolymer comprising 4-hydroxybutyrate units. It may be referred to herein as P4HB, PHA4400 or TephaFLEX™ biomaterial (manufactured by Tepha Inc., Cambridge, Mass.).

"Copolymers of poly-4-hydroxybutyrate" as generally used herein means any polymer comprising 4-hydroxybutyrate with one or more different hydroxy acid units.

II. Fibers

A. Polymers

The filament may be formed from biodegradable polymers, such as poly-4-hydroxybutyrate (P4HB), and copolymers thereof, such as poly-4-hydroxybutyrate-co-poly-3-hydroxybutyrate (P4HB-P3HB) and poly-4-hydroxybutyrate-co-poly (glycolic acid) (P4HB-PGA). Tepha, Inc. of Cambridge, Mass. produces poly-4-hydroxybutyrate and copolymers thereof using transgenic fermentation methods.

B. Methods of Making Non-Curling Fibers

Methods of producing non-curling fibers with knot strength as high as 10 kg and improved straight to knot conversions (ratio of knot strength to tensile strength) have been developed. A polymer such as PHA4400 or copolymers thereof, is dried. Dried pellets of the polymer are melt extruded, then stretched in order to effect its orientation and thereby increase its tensile strength. The oriented fiber is then constrained between two godets and a heating media. The second godet rotates at a lower speed than the first, thereby allowing the fiber to shrink and relax. A third godet may be utilized before winding the fiber material. The relaxation step is carried out at a temperature from about 30 to about 150° C. In carrying out the annealing operation, the desired length of fiber may be wound around a creel, rack or skein and the wound material placed in a heating media maintained at the desired temperature to anneal the fiber. The annealing step is carried out at a temperature from about 35 to about 150° C. After a suitable period of residency in the heating media, the annealed fiber is then removed from the heating media and unwound. The resultant fiber is curl free, more pliable, has a higher knot strength and knot security.

In a preferred method, polymer fibers with improved handling and less tendency to curl are prepared by extruding the fiber, as described above, and then treated with an aging step whereby partially drawn polymer filament is stored from 2 to 72 hours at a temperature between 0 and −80° C. before processing with relaxation and annealing, as described above.

In yet another preferred method, polymer fibers with improved handling are prepared by blending up to 15% by weight calcium stearate, calcium phosphate or similar materials into the polymer and then melt extruding the polymer into the desired filaments. The filaments may be further processed through relaxation and annealing, as described above.

C. Filament Properties

Filaments prepared according to these methods are characterized by the following physical properties: (i) elongation to break from about 17% to about 85% (ii) Young's modulus of less than 350,000 psi, (iii) knot to straight ratio (knot strength/tensile strength) of 55-80%, or (iv) load to break from 1100 to 4200 g. These fibers exhibit a reduced tendency to curl and better knot and handling characteristics.

II. Applications for Non-curling Filaments

The filaments can be used to form a wide range of medical products, including suture materials, stable surgical meshes, synthetic ligament and tendon devices or scaffolds. These fibers, both monofilament and multifilament, can be used to manufacture sutures with prolonged strength retention, as well as fiber-based medical devices such as surgical meshes and braids. Properties that can be improved through the use of these methods to decrease curling are lower Young's Modulus and an increase in straight to knot conversion. Modulus values are important to surgeons since soft, highly flexible sutures are easier to handle, use and tie. Flexible and slightly elastic sutures are also desirable since they conform to the wound and permit latitude in the tension applied to the suture by the surgeon.

The suture materials may be useful in the treatment of patients with diabetes, obesity, nutritional impairment, compromised immune systems, or other conditions such as malignancy or infection that compromise wound healing.

Stable surgical meshes can be used in procedures, such as pelvic floor reconstruction, urethral suspension (to prevent stress incontinence using the mesh as a sling), pericardial repair, cardiovascular patching, cardiac support (as a sock that fits over the heart to provide reinforcement), organ salvage, elevation of the small bowel during radiation of the colon in colorectal cancer patients, retentive devices for bone graft or cartilage, guided tissue regeneration, vascular grafting, dural substitution, nerve guide repair, as well as in procedures needing anti-adhesion membranes and tissue engineering scaffolds.

Further uses include combinations with other synthetic and natural fibers, meshes and patches. For example, the absorbable fibers and devices such as meshes and tubes derived from the fibers can be combined with autologous tissue, allogenic tissue, and/or xenogenic tissue to provide reinforcement, strengthening and/or stiffening of the tissue. Such combinations can facilitate implantation of the autologous, allogenic and/or xenogenic tissue, as well as provide improved mechanical and biological properties. Combination devices can be used, for example, in hernia repair, mastopexy/breast reconstruction, rotator cuff repair, vascular grafting/fistulae, tissue flaps, pericardial patching, tissue heart valve implants, bowel interposition, and dura patching.

The present invention will be further understood by reference to the following non-limiting examples.

EXAMPLE 1

Melt Extrusion of PHA 4400

PHA4400 (Tepha, Inc., Cambridge, Mass.) (Mw 575K) was ground into small pieces using a Fritsch cutting mill (Pulversette 15, 10 mm bottom sieve) and dried under vacuum overnight to less than 0.01% (w/w) water. Dried pellets of the polymer were fed into an extruder barrel of an AJA (Alex James Associates, Greer, S.C.) ¾" single screw extruder (24:1 L:D, 3:1 compression) equipped with a Zenith type metering pump (0.16 cc/rev) and a die with a single hole spinnerette (0.026", 2:1 L:D) under a blanket of nitrogen. The 4 heating zones of the extruder were set at 140°, 190°, 200° and 205° C. The extruder was set up with a 15 ft drop zone, 48" air quench zone (10° C.), a guide roll, three winders and a pickup. The fiber was oriented in-line with extrusion by drawing it in a multi-stage process to provide fiber with high tensile strength and a reduced extension to break. The fiber was drawn in-line to stretch ratios of 6 to 11×. A spin finish (Goulston, Lurol PT-6A) was dissolved in isopropanol at 10% (v/v) and applied to the fiber before the first roll to act as a lubricant and protect the fiber during downstream processing. Molten polymer was then passed through a heated block to a metering pump and extruded from a die with a single hole spinneret. The block, metering pump and the die were maintained at a constant temperature, preferably 180-250° C. Pump discharge pressure was kept below 1500 psi by controlling the temperatures and the speed of the metering pump. The resulting spun extrudate filament was free from all melt irregularities. The extrudate was then drawn in a heated tube, which was maintained at a temperature above the melting temperature of the filament, quenched in a water bath, drawn through multistage orientation, and hot stretched, using a heated tube oven or hot liquid, preferably water, without the filament touching any surface until it is naturally cooled.

The highly oriented fiber passes through another heating unit maintained at a temperature from about 30° C. to about 150° C. The second heat treatment results in online relaxation, or shrinkage of the fiber. In order to accommodate this online shrinkage the exit fiber speed is allowed to be less than the feed speed by as much as 40%.

The relaxed fiber was wound on creels or racks and annealed for a preset time in an annealing media maintained at temperature from about 35° C. to about 150° C. After annealing, the fiber was allowed to reach room temperature and tested.

EXAMPLE 2

Characteristics of Sutures prepared in Example 1

Tensile mechanical properties of the melt extruded fibers were determined using a universal mechanical tester.

The mechanical properties of monofilament sutures prepared from non-curling fibers are shown in Table 1.

TABLE 1

Mechanical Properties of Monofilament Sutures Prepared from Non-Curling Fibers

| Size | Diameter mm | Load at Break g | Knot Tensile kg | Elongation % | Young's Modulus Psi |
|---|---|---|---|---|---|
| 3/0 | 0.278 | 4148 | 2.95 | 60 | 101,590 |
| 5/0 | 0.166 | 1800 | 1.31 | 64 | 123,600 |
| 6/0 | 0.105 | 1100 | — | 22 | 310,000 |

Surgical meshes were prepared with the sutures. Fabric construction was as follows: Mach #30 Raschel Knit 36 gauge fabric, 150 ends, 16 courses, 40 stitches per inch, using 18 needles per inch. Specifications for the finished fabric were: Weight: 58 g/m$^2$ (1.72 oz/sq. yard), Thickness: 0.29 mm.

The mechanical properties of surgical meshes knitted from non-curling fibers are shown in the Table 2.

TABLE 2

Mechanical Properties of Surgical Meshes Knitted from Non-Curling Fibers

| Samples Construction | Width (mm) | Thickness (mm) | Ball Burst (kg) | Extension at Peak (mm) | # Pores Per cm$^2$ | Density g/m$^2$ | Load per Density |
|---|---|---|---|---|---|---|---|
| No. 1 4 mil | 44.45 | 0.583 | 37.5 | 33.2 | 60 | 99 | 0.38 |
| No. 2 4 mil | 44.45 | 0.464 | 23.0 | 30.6 | 25 | 56 | 0.41 |
| No. 3 4 mil | 44.45 | 0.559 | 44.3 | 36.5 | 240 | 128 | 0.35 |
| No. 4 4 mil | 44.45 | 0.626 | 52.5 | 35.4 | 161 | 135 | 0.39 |
| No. 5 6 mil | 44.45 | 0.565 | 42.0 | 34.5 | 144 | 121 | 0.35 |

Those skilled in the art will recognize, or be able to ascertain using no more than routine experimentation, many equivalents to the specific embodiments of the invention described herein. Such equivalents are intended to be encompassed by the following claims.

I claim:

1. A method of making a polyhydroxyalkanoate filament comprising 4-hydroxybutyrate or copolymers thereof comprising
   a) drying the water content of polyhydroxyalkanoate pellets comprising 4-hydroxybutyrate or copolymers thereof to less than 0.01% (w/w);
   b) feeding the dried polyhydroxyalkanoate pellets into an extruder barrel under a blanket of nitrogen to melt the polyhydroxyalkanoate;
   c) passing the molten polyhydroxyalkanoate through a heated block to a metering pump;
   d) extruding the polyhydroxyalkanoate from a die with a single hole spinneret to produce a spun extrudate filament;
   e) drawing the spun extrudate filament into a heat zone, maintained at a temperature above the melting temperature of the filament,
   f) orienting and relaxing the filament,
   g) constraining the filament during orientation and relaxation to shrink the filament, and
   h,) annealing the filament, to produce a polymeric filament comprising 4-hydroxybutyrate or copolymers thereof, wherein the filament has an elongation to break from 17% to 85%, a Young's modulus of less than 350,000 psi, or a load at break between 1100 and 4200 g, and is produced by extrusion, orientation, relaxation and annealing of the extruded filament.

2. The method of claim 1 further comprising an aging step wherein the extruded polyhydroxyalkanoate filament is partially drawn and is stored for a time period ranging from 2 to 72 hours at a temperature between 0 and −80° C.

3. The method of claim 1 further comprising prior to step a) blending into the polyhydroxyalkanoate an additive selected from the group consisting of calcium stearate and calcium phosphate, wherein the additive comprises up to 15% (w/w) of the polyhydroxyalkanoate blend.

4. The method of claim 1 further comprising forming the filament into a suture.

5. The method of claim 1 further comprising forming the filament into a mesh.

6. The method of claim 1 further comprising forming the filament into a medical device.

7. The method of claim 6 comprising forming the filament into a device for repair of tendons or ligaments.

* * * * *

UNITED STATES PATENT AND TRADEMARK OFFICE
CERTIFICATE OF CORRECTION

| | | |
|---|---|---|
| PATENT NO. | : 7,641,825 B2 | Page 1 of 1 |
| APPLICATION NO. | : 11/193580 | |
| DATED | : January 5, 2010 | |
| INVENTOR(S) | : Said Rizk | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 970 days.

Signed and Sealed this

Sixteenth Day of November, 2010

David J. Kappos
*Director of the United States Patent and Trademark Office*